(12) United States Patent
Victor et al.

(10) Patent No.: US 8,454,608 B2
(45) Date of Patent: Jun. 4, 2013

(54) DISPOSABLE FLEX REAMER

(75) Inventors: Gary Victor, Wheatfield, NY (US); Patrick W. White, West Chester, PA (US)

(73) Assignee: Greatbatch Ltd., Clarence, NY (US)

( * ) Notice: Subject to any disclaimer, the term of this patent is extended or adjusted under 35 U.S.C. 154(b) by 226 days.

(21) Appl. No.: 12/961,565

(22) Filed: Dec. 7, 2010

(65) Prior Publication Data

US 2011/0144649 A1 Jun. 16, 2011

Related U.S. Application Data (60) Provisional application No. 61/286,487, filed on Dec. 15, 2009.

(51) Int. Cl.
*A61B 17/16* (2006.01)
*B23D 71/08* (2006.01)

(52) U.S. Cl.
USPC .............................. 606/80; 408/231; 408/713

(58) Field of Classification Search
USPC .............. 606/79, 80, 180; 408/211, 227, 229, 408/231, 233, 713
See application file for complete search history.

(56) References Cited

U.S. PATENT DOCUMENTS

| 1,957,348 | A | * | 5/1934 | Miller et al. ................... 408/186 |
| 4,706,659 | A | | 11/1987 | Matthews et al. |
| 5,122,134 | A | | 6/1992 | Borzone et al. |
| 5,976,137 | A | * | 11/1999 | Mayer ............................. 606/62 |
| 6,258,093 | B1 | | 7/2001 | Edwards et al. |
| 6,887,172 | B2 | | 5/2005 | Arasmith |
| 6,918,913 | B2 | | 7/2005 | White |
| 6,949,101 | B2 | | 9/2005 | McCleary et al. |
| 7,513,899 | B2 | | 4/2009 | Grim |
| 2004/0236339 | A1 | | 11/2004 | Pepper |
| 2005/0096685 | A1 | * | 5/2005 | Murphy et al. ................ 606/180 |
| 2007/0276394 | A1 | * | 11/2007 | Johnson et al. ................. 606/80 |
| 2008/0125783 | A1 | * | 5/2008 | Perez-Cruet et al. ........... 606/82 |
| 2008/0195101 | A1 | | 8/2008 | Lechot et al. |
| 2010/0145342 | A1 | | 6/2010 | Grace et al. |

OTHER PUBLICATIONS

European Search Report dated May 20, 2011.

* cited by examiner

*Primary Examiner* — Kevin T Truong
*Assistant Examiner* — Christian Sevilla
(74) *Attorney, Agent, or Firm* — Steven W. Winn (57) ABSTRACT

A single use intramedullary reamer comprised of a reamer head assembly and a reamer shaft. The reamer head assembly further comprising a series of reamer blades that reside in a series of surface slots that are helically oriented around the cylindrical body. The series of reamer blades are bonded with the cylindrical body through induction bonding.

30 Claims, 9 Drawing Sheets

DISPOSABLE FLEX REAMER

CROSS-REFERENCE TO RELATED APPLICATIONS

This application claims priority from U.S. Provisional Patent Application Ser. No. 61/286,487, filed Dec. 15, 2009.

FIELD OF THE INVENTION

The present invention relates to the art of orthopedic reamers, and more particularly, to a disposable flexible reamer used for intramedullary reaming.

PRIOR ART

Reamers are tools used in orthopedic procedures to cut bone and associated tissue matter. Specifically, flexible reamers of the present invention are designed to cut and bore into the intramedullary space or inner canal of a long bone such as a femur, tibia or humerus. Typically, the intramedullary space of a long bone is reamed to clean and create a space for an implant. As such, these reamers are required to be sterile and sharp. Using a dull reamer generates heat that typically leads to tissue necrosis and results in undesirable patient outcomes. A non-sterile reamer blade typically results in an infected and damaged intramedullary space that may lead to other problems for the patient.

Reamers are often used in trauma procedures. In one such procedure, a prosthetic implant is inserted into the intramedullary space to help mend a fractured bone. In the procedure, a flexible reamer is first inserted into the intramedullary space of the fractured bone. Using the flexible reamer, a cavity space is then formed for insertion of the implant into the fractured bone.

Prior to the reaming process, a guide wire is typically inserted into the intramedullary space. The reamer is then passed over the guide wire and inserted into the intramedullary space for enlarging. The intramedullary space is enlarged incrementally with a series of reamers. A separate interchangeable reamer is required for each step. This requires that each reamer be extracted from the intramedullary space and slid off the guide wire. The next incremental reamer is then passed over the guide wire and advanced into the intramedullary space. This procedure could involve as many as 10 to 15 interchanges.

Currently, orthopedic reamers are typically fabricated as modular units that are sold in a set of an array of diameters. These reamer tool sets are manufactured with reamer cutting heads providing bore sizes ranging from about 6 mm to about 28 mm in 0.5 mm increments sometimes totaling over 25 sizes. Since it is desirable to achieve a close prosthetic fit, a wide array of reaming tools of varying sizes are required to be at hand to provide the most precise cut and optimum bore diameter.

Reamers have historically comprised two components, a one-piece reamer cutting head and a reamer shaft that connects to the reamer head assembly. The one-piece reamer cutting head is machined from a single block of metal into a hollow cylinder incorporated with a series of protruding blades that emerge from the outer surface of the cylinder.

Currently, reamer cutting heads are typically manufactured from a single piece of biocompatible metal. Traditional reamer cutting heads are fabricated using intricate precision machining techniques that create the central cylinder and the series of protruding reamer blades. This manufacturing process is time consuming and is not cost effective.

Because of their high cost, traditional cutter heads are typically reused multiple times. Over time, as these reamer heads are used and reused, the cutting blades become dull. Therefore the reamer cutting blades are required to be resharpened and sterilized before each reuse. However, this resharpening and sterilization process adds additional cost and increases the possibility of infection. There is a high likelihood that the sterilization process may not remove all possible infection agents such as bacteria, machining lubricants, and the like.

Often times reamers are used for surgical procedures for which they are not intended. In many cases, the nearest available tool is often used to perform the procedure whether or not it is designed or intended for such use. For example, a set of reamer heads dedicated for intramedullary space reaming, may be used for a cemented hip revision. In this procedure, the reamer cutting head is used to cut away old cement instead of bone. Hip replacement cement tends to be more abrasive than bone, which, therefore increases the wear and stress on the cutting surface. Using these reamer cutting tools to cut into hip replacement cement, typically results in excessive wear of the reamer cutting blade surface which hastens blade degradation. As a result, the tool becomes an ineffective reaming tool. The sharpness of the cutting blade is diminished and the structural soundness of the cutting blade is weakened.

Unfortunately there is no simple way to evaluate cutting efficiency after these reamer tools have been used and reused, especially after use in procedures for which they are not intended. Many times it isn't until the surgeon uses the reamer again that they become aware that the reamer is cutting incorrectly. In many cases an ineffective, dull, or contaminated reamer tool is not detected until well into the reaming procedure or even after the procedure is complete. Good surgical outcomes are largely dependent on the use of a sharp, sterile reamer that is in optimal condition. Poor surgical outcomes such as a damaged intramedullary space, can occur as a result of using dull or contaminated reamers.

The geometry of the reamer cutting blade is a major contributor to the sharpness and cutting efficiency of the tool. It is well known in the art that cutting tools with helical flutes are more efficient at cutting bone than straight flutes. Typically helical flutes are manufactured using a grinding process to form them from a solid metal core. Due to the high cost of the process, these tools are typically reused multiple times.

Examples of helical ground flutes are shown in U.S. Pat. No. 6,258,093 to Edwards which discusses the importance of flute shape, helix angle and grooves on cutting efficiency. Edwards mentions the use of a premolded blank and points out that the flute depth is also an important aspect for debris removal which in turn relates to efficiency.

However, due to their intricate design of grooves and teeth, the embodiments disclosed by Edwards are prone to the same resharpening and sterilization problems that have been previously discussed.

Furthermore, the reamer blade assembly of the present invention has a feature that allows for increased intramedullary debris removal and reaming efficiencies. This feature, which will be discussed in more detail, is based on an optimal shape and positioning of the insert reamer blades about the cylindrical body of the assembly. This feature is not present nor taught by Edwards or disclosed in the prior art.

Reamers have also been made of coiled wire. These prior reamer designs are also prone to cleanliness and structural integrity issues. Often times debris becomes entrapped in the springs which are problematic to clean in addition, these earlier coiled wire reamers often become unwound when driven in the reverse direction.

Accordingly, the present invention provides a cost effective single use flexible intramedullary reamer with a novel blade and assembly head design that improves cutting efficiency. The enhanced reaming efficiencies of the present invention decrease procedural times and minimize patient trauma. The intramedullary reamer of the present invention ensures sharpness and cleanliness that promotes optimal patient outcomes.

SUMMARY OF THE INVENTION

The present invention provides a disposable reamer comprising a reamer head assembly and a reamer shaft. The reamer head assembly further comprises a cylindrical body and a series of insert reamer blades which are attached to the outside surface of the cylindrical body. The cylindrical body is universal and can be preferably manufactured with a hollow core to allow clearance for the passage of a guide wire and/or intramedullary debris. Formed into the cylindrical body are slots which extend along the outer surface of the body. These slots are adapted to receive a series of insert reamer blades. Each blade is arranged with a preferred separation distance and helical orientation along the outer surface of the body.

Each insert reamer blade is comprised of a reamer blade attachment portion and a reamer blade cutting portion. The reamer blade attachment portion has a bottom edge and engagement openings for mating with the slot. The cutting portion of the blade further comprises a forward blade surface, a bone cutting surface, and a rearward relief surface. A transition line extending along a longitudinal axis of the blade body partitions the blade attachment portion from the reamer blade cutting portion. Each blade is bent about this transition line. When fully assembled, the angled reamer blades create a helical cutting path as they are rotated.

Each blade is placed in the cylindrical body such that the bottom edge of the blade attachment portion resides in the slot with the blade cutting portion protruding from the outer surface of the body. Each blade is further oriented with its forward blade surface positioned towards the distal end of the cylindrical body. In addition, each reamer blade is positioned about the outer surface of the cylindrical body at an optimum separation distance from adjacent reamer blades. This optimal separation distance allows for unobstructed flow of intramedullary debris over the cylindrical body which results in increased blade stability and efficiency.

When correctly positioned in the slot, the forward surface of the blade initially begins to bore into the intramedullary space. The positively sloping surface of the forward blade surface pushes the intramedullary material to the bone cutting surface, which in turn cuts through the intramedullary tissue matter. The bone cutting surface is positioned proximal of the forward blade surface. The negatively sloped rearward relief surface serves to stabilize the blade as it bores deeper into the intramedullary space. The sloping surface of the rearward relief surface also enables the reamer to cut through tissue when traversing in the reverse direction.

During the manufacturing process, each blade is engaged in their respective cylinder slot. Once positioned in the slots, the blades are bonded to the cylindrical body via an induction heating process. During this induction heating process, the reamer head assembly is subjected to a heat source which melts the surrounding material of the cylindrical body. The melted material flows into the slot, covering the surface of the blade attachment portion. The flowing molten material then penetrates through the blade engagement openings, creating a fluid connection between the cylindrical body and the insert reamer blade, thereby bonding each blade with the body. This low cost production process avoids the need for expensive grinding operations and can use simple stamping or chemical etching to form the insert blades.

Each slot is designed with a compound angle which further positions the reamer blade in a preferred helical orientation. The compound slot angle helps impart a twisting motion from the forward blade cutting surface to the rearward relief blade surface when the blade is rotated through the intramedullary space. Therefore, the combination of the compound slot angle with the reamer blade bend creates an efficient and effective reamer cutting tool.

In addition to the reamer head assembly, a reamer shaft can also be provided. This reamer shaft can be provided with a removable interference fit, a locking junction, or can be designed as an integral portion of the reamer.

DETAILED DESCRIPTION OF THE PREFERRED EMBODIMENTS

Now turning to the figures, illustrated in FIGS. 1-4 is a cylindrical body 10. This cylindrical body 10 forms the central foundation to which each reamer blade 34 of the present invention is attached. The cylindrical body 10 has a length, a thickness and an outer diameter. The cylindrical body 10 can be made of a solid construction. However, in a preferred embodiment, the body 10 can be constructed with a central passageway 12 that extends longitudinally through the thickness and along the length of the body 10 from a proximal end portion 16 to the distal end 14. This central passageway 12 allows for the insertion of a guide wire (not shown) and allows for the passage of debris that is removed from the intramedullary space. It is contemplated that a vacuum tube could be inserted into the passageway 12 to remove debris. It is preferred that the length of the cylindrical body 10 ranges from about 1.0 mm to about 20.0 mm and that the outer diameter ranges from about 1.0 mm to about 15.0 mm. It is also preferred that the diameter of the passageway 12 ranges from about 0.5 mm to about 5.0 mm. The cylindrical body 10 is made of a biocompatible material, preferably a moldable biocompatible polymeric material. Preferred polymeric materials include, but are not limited to, polyetheretherketone (PEEK), polyarylamide (PARA) and acrylonitrile butadiene styrene (ABS).

Formed into the outer surface 18 of the cylindrical body 10 are a series of slots 20. In a preferred embodiment, each slot 20 has a slot width 15 and a slot depth 17 sized to receive a reamer blade insert 34. Each slot 20 has a slot length 19 that extends from a proximal end portion 16 of the cylindrical body 10 to a portion of the distal end 14. It is also preferred that each slot 20 is formed partially cut into the cylindrical body 10 such that the slot depth 17 does not penetrate into the central passageway 12.

Figure 3:
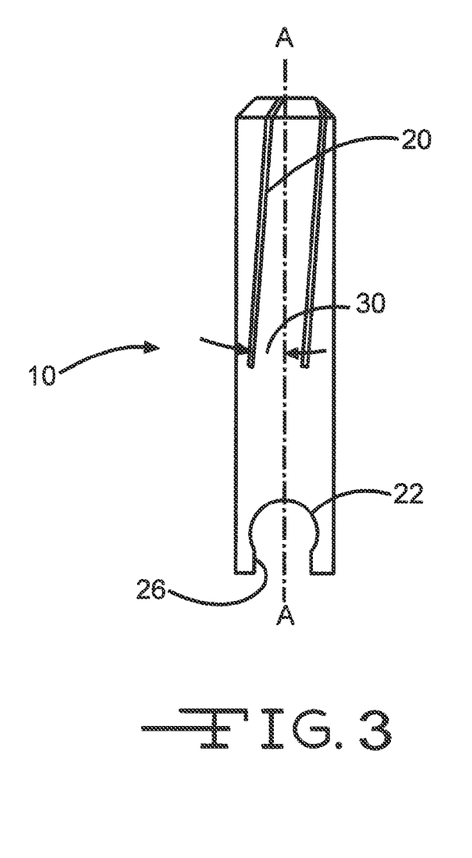
FIGS. 3 and 4 are side views taken from the side of the cylindrical body of the present invention.
Figure 4:
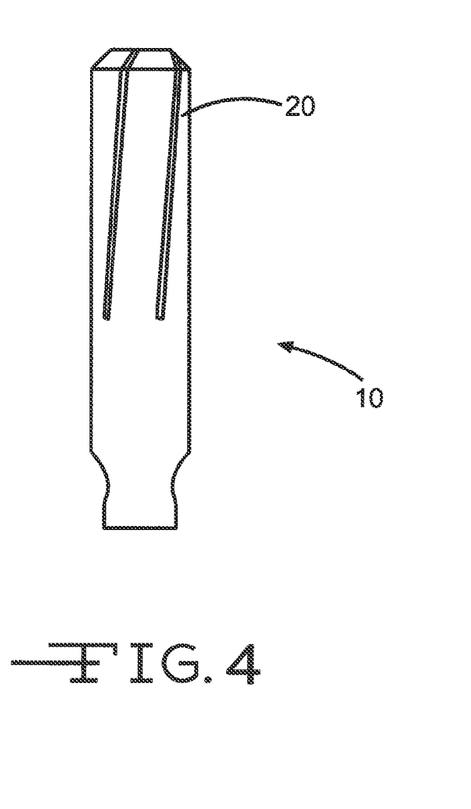

In a preferred embodiment, slot 20 is fabricated with a compound angle. The compound angle comprises a first slot angle 30 and a second slot angle 32. As shown in FIG. 3, the first slot angle 30 is measured with respect to longitudinal axis A-A. The first slot angle 30 is the angle at which the length 19 of slot 20 deviates from the longitudinal axis A-A as it extends along the outer surface 18 of the cylindrical body 10. It is preferred that the first slot angle 30 deviates from longitudinal axis A-A by about 3° to about 30°.

Figure 2:
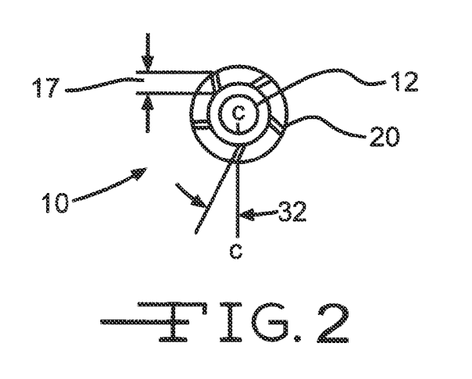
FIG. 2 is an end view of the distal end portion of the cylindrical body of the present invention.

The second slot angle 32 is the angle at which slot 20 is cut into the surface of the cylindrical body 10. As shown in FIG. 2, the second slot angle 32 is measured with respect to perpendicular axis C-C which extends from the outer surface 18 of the cylindrical body 10 perpendicular to the longitudinal axis A-A. It is preferred that the second slot angle 32 deviates from the perpendicular axis by about 5° to about 45°.

The compound angles 30, 32 of cylindrical body 10 of the present invention are designed such that when each reamer blade 34 is positioned in a slot 20, the blade cutting portion 40 (FIG. 9) follows a helical path as it penetrates into the intramedullary space.

Alternatively, cylindrical body 10 can be fabricated with a slot 20 that does not have a compound angle. In this alternatively preferred embodiment, the cylindrical body 10 is constructed with a slot 20 with a first slot angle 30. Slot angle 30, similarly to the previous embodiment, has a slot length 19 that extends from a proximal end portion 16 to the distal end 14.

Figure 1:
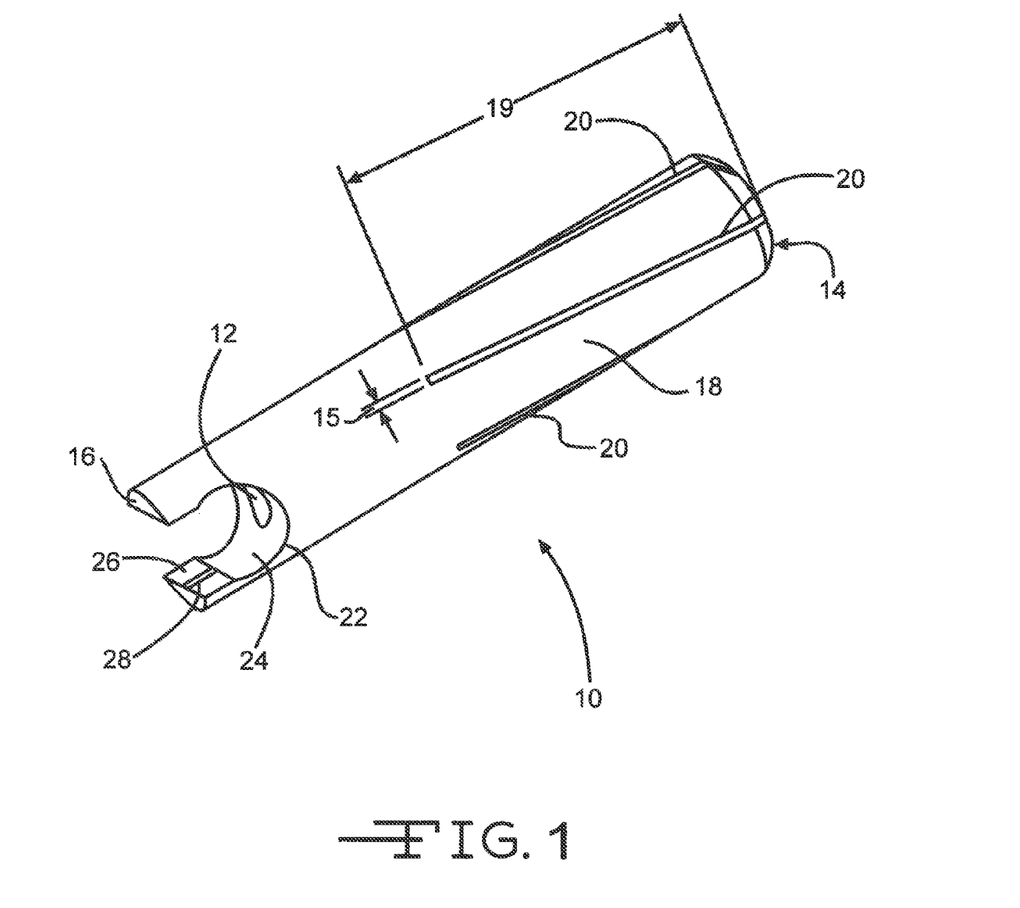
FIG. 1 is a perspective view of the cylindrical body of the present invention.
Figure 10:
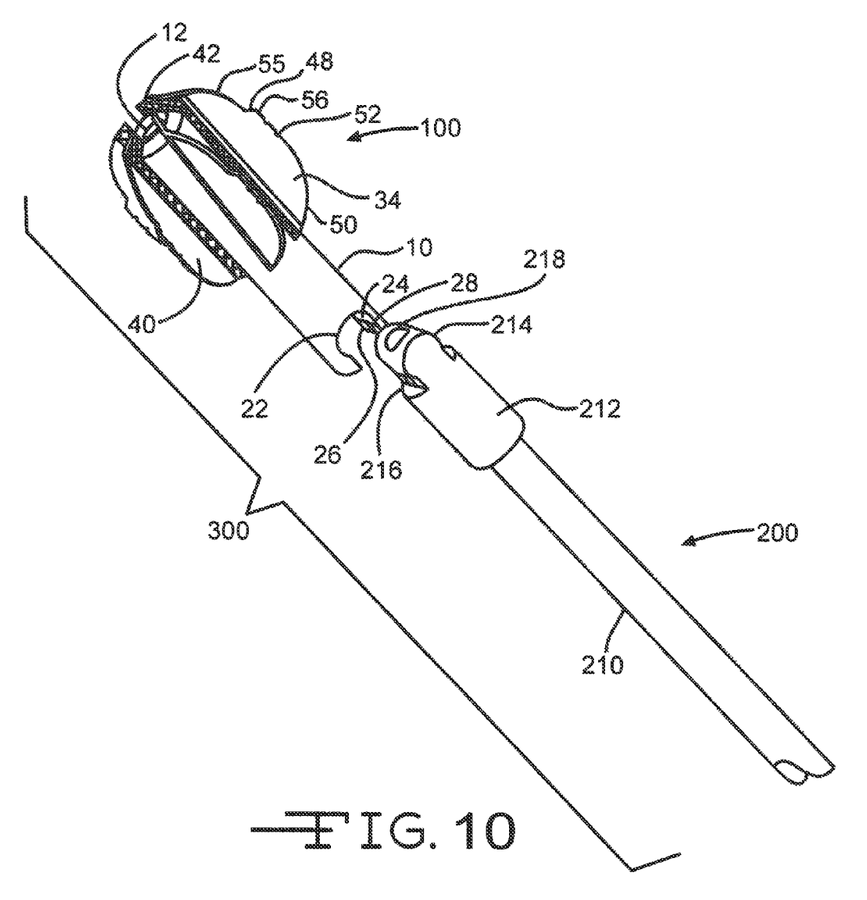
FIG. 10 illustrates a perspective view of a preferred embodiment of the reamer shaft of the present invention.
Figure 11:
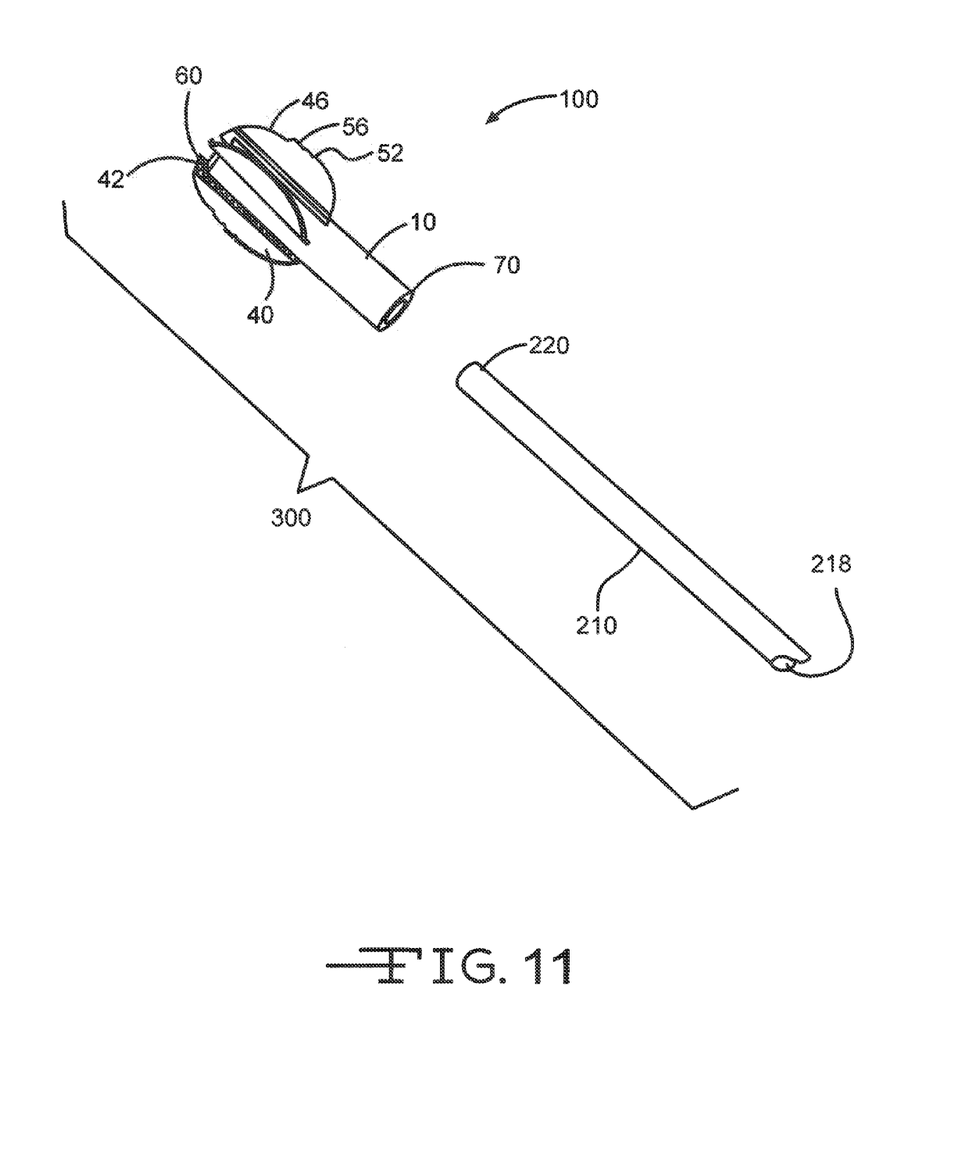
FIG. 11 illustrates a perspective view of an alternate embodiment of the reamer shaft of the present invention.

In a preferred embodiment, shown in FIG. 1, the proximal end 16 of the cylindrical body 10 has a dovetail interface 22 that comprises a female radius 24 and flats 26. This dovetail interface 22 is designed to receive and lock into place a corresponding dovetail male end 214 of a reamer shaft 200 (FIG. 10). The flats 26 have a preferred groove 28 that provides for a quick connect mechanism described in White U.S. Pat. No. 6,918,913 of the present inventor, the entire contents of which are incorporated by reference herein.

The corresponding distal male end 214 of the reamer shaft 200 (FIG. 10) slides into the dovetail interface 22 located at the proximal end portion 16 of the cylindrical body 10. The interface of these two features provides a quick means of locking and releasing the reamer head assembly 100 to the reamer shaft 200. However, it is contemplated that the proximal end 16 of the cylindrical body 10 could be constructed as a continuation of the hollow cylindrical body 10. The reamer shaft 200 could then be inserted into the hollow proximal end 16 of the body 10.

Figure 5:
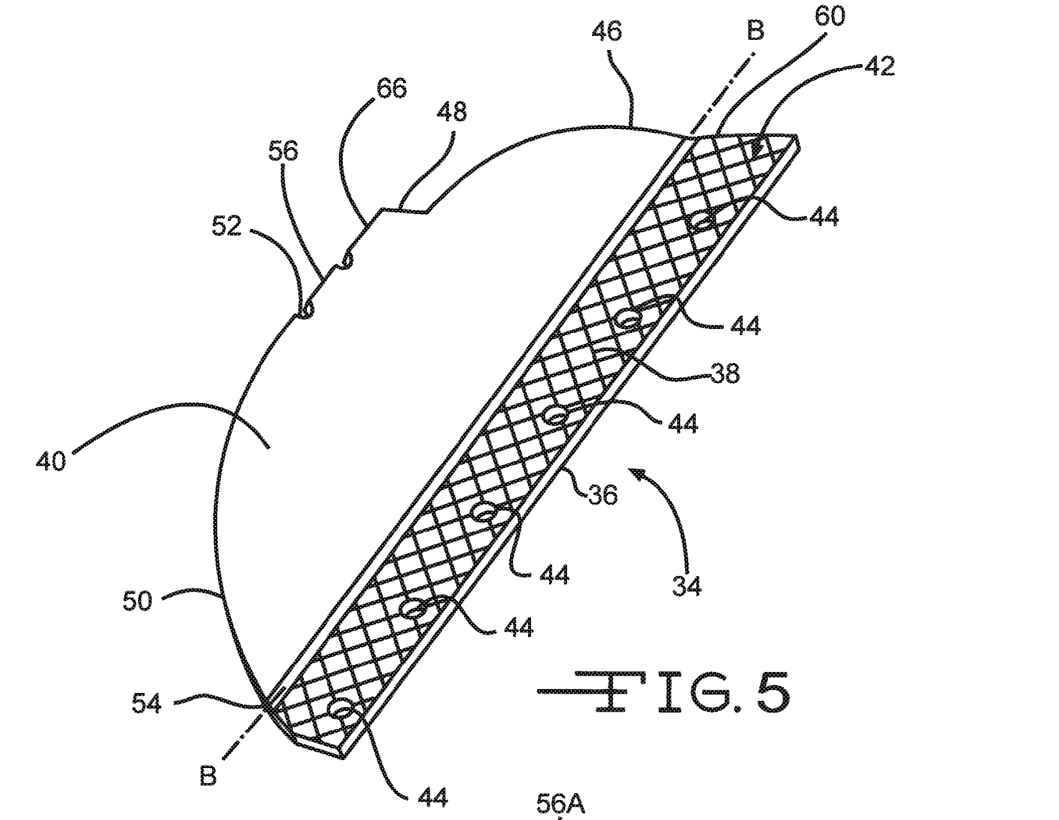
FIGS. 5 and 5A are perspective and plane illustrations, respectively, of preferred embodiments of the insert reamer blade of the present invention.

FIG. 5 illustrates a preferred embodiment of an insert reamer blade 34 of the present invention. Blades 34 are preferably constructed from biocompatible metals such as stainless steel. Other preferred metals include, but are not limited to, 316 stainless steel, MP35N, titanium, and combinations thereof.

In the preferred embodiment illustrated in FIG. 5, the reamer blade 34 has a continuous blade surface comprising an attachment portion 38 and a blade cutting portion 40. The two portions 38, 40 are partitioned by a transition line 54 that extends along longitudinal axis B-B. Transition line 54 serves as a boundary that partitions the attachment portion 38 from the blade cutting portion 40. In addition, as will be explained in more detail, transition line 54 also serves as the line about which blade 34 is bent.

The attachment portion 38 further comprises a planar rectangular surface 42 with a bottom edge 36 with forward facing side edge 60. The bottom edge 36 extends parallel to the blade longitudinal axis B-B and serves as the surface that interfaces with the bottom of slot 20. The bottom edge 36 has a thickness that preferably ranges from about 0.5 mm to about 10 mm.

It is preferred that planar surface 42 comprises a roughened finish and a series of engagement openings 44 that aid in the induction bonding process. During the induction bonding process, molten polymeric material of the body 10, flows through the engagement openings 44, creating a fluid connection between the cylindrical body 10 and reamer blade 34. Once the molten polymeric material hardens, the reamer blade 34 becomes securely anchored to the body 10.

The blade cutting portion 40 comprises a forward cutting surface 46, a bone cutting surface 48 and a rearward relief surface 50. As illustrated in FIG. 5, in a preferred embodiment, the cutting portion 40 extends seamlessly from the forward blade surface 46, located at a distal end of the reamer blade to the rearward relief surface 50, located at a proximal end of the reamer. The bone cutting surface 48 is disposed between the forward cutting surface 46 and the rearward relief surface 50.

The forward cutting surface 46, the bone cutting surface 48 and the rearward relief surface 50 are provided along the outer perimeter of the blade cutting portion 40 of the reamer blade 34. In the preferred embodiment illustrated in FIG. 5, the forward cutting surface 46 and the rearward cutting surface 50 have rounded or convex surfaces.

The bone cutting surface 48 fluidly transitions from the forward cutting surface 46 to the rearward relief surface 50. It is preferred that the bone cutting surface 48 forms an angle that ranges from about 40° to about 50°, most preferably about 45°, with respect to the blade longitudinal axis B-B. It is also preferred that the forward cutting surface 46 and bone cutting surface 48 have a sharp edge with a blade thickness 35 (FIGS. 8 and 9) that ranges from about 0.1 mm to about 5.0 mm.

Figure 5A:
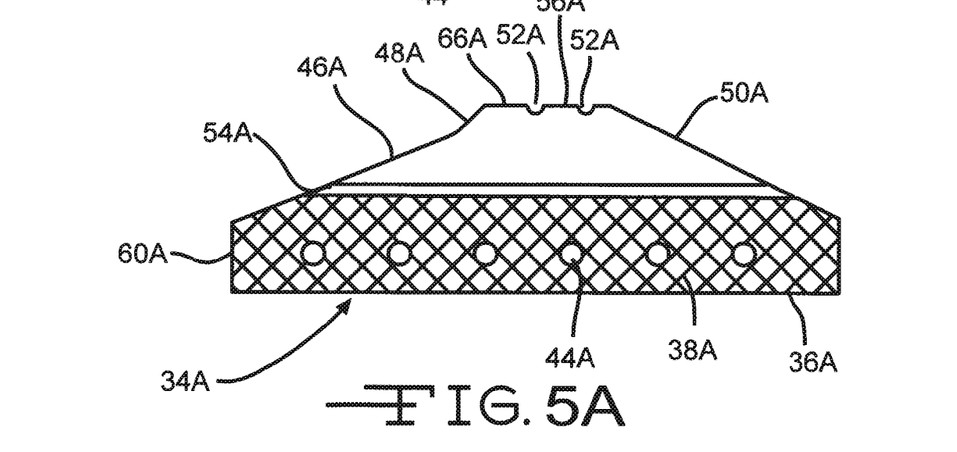

In an alternate embodiment shown in FIG. 5A, the reamer blade 34A may be fabricated in a shape that is similar to that of a triangle. Unlike the cutting portion 40 shown in FIG. 5, the alternate embodiment shown in FIG. 5A, has a forward cutting surface 46A and a rearward relief surface 50A that are not rounded. More specifically, the alternate embodiment of the cutting portion 40A shown in FIG. 5A is comprised of a forward cutting surface 46A and a rearward relief surface 50A that have angled straight edges. The angles forming the forward cutting surface 46A and the rearward relief surface 50 are measured with respect to bottom edge 36A. It is preferred that the forward cutting surface 46A is angled from about 10° to about 65° with respect to bottom edge 36A. It is also preferred that the rearward relief surface 50 is angled from about 100° to about 170° with respect to bottom edge 36A.

Referring back to FIG. 5, the blade cutting portion 40 is designed to cut a round cavity in the intramedullary space of a bone. To increase the cutting efficiency, a groove or notch 52 is positioned through a portion of the edge of the blade cutting portion 40. At least one notch 52 is provided proximal of the bone cutting surface 48. Preferably the notch 52 is cut through a flat portion 56 of the outer edge of the blade cutting portion 40. This planar surface 56 extends between the bone cutting surface 48 and the rearward relief surface 50 (relief surface 50A in FIG. 5A). Planar surface 56 acts as a blade 34 stabilizer, minimizing lateral motion of the reamer blade 34 as it penetrates through the intramedullary space. Alternatively the notch 52 may be cut through the edge of a portion of the rearward cutting surface 50.

Preferably, the forward cutting surface 46 is configured to initiate an opening into the intramedullary space or bone canal. Once the opening in the intramedullary space has been initiated, the bone cutting surface 48 begins to cut the bone and tissue material. The bone cutting surface 48 is fabricated to efficiently cut through the material of the intramedullary space so as to create a bored hole with a smooth internal cavity surface. The rearward relief surface 50 acts to stabilize the reamer blade 34. The rearward relief surface 50 of the reamer blade 34 extends from the flat 56 or bone cutting surface 48 to the proximal end of the blade 34. The rearward relief surface 50 stabilizes the rotation of the reamer blade 34 as it bores through the intramedullary space. A stabilized reamer head assembly 100 contributes to a reamed cavity with a smooth internal surface. The rearward relief surface 50 can be fabricated with a rounded surface as shown in FIG. 5 or alternatively can be fabricated with a straight angled surface as shown in FIG. 5A.

Figure 6:
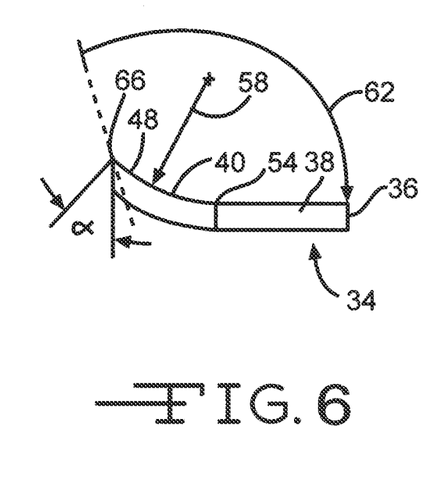
FIGS. 6 and 6A are illustrations of the insert reamer blade of the present invention showing examples of preferred bend angles.
Figure 6A:
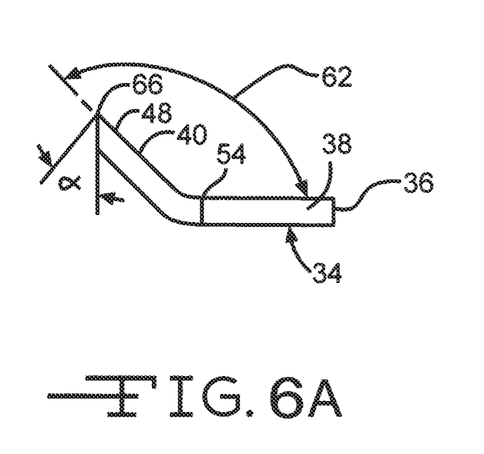

In a preferred embodiment, the reamer blade 34 is bent along transition line 54 such that the plane of the cutting portion 40 deviates from the plane of the attachment portion 38. Each reamer blade 34 is bent along the transition line 54 such that the blade cutting portion 40 and the blade attachment portion 38 are not coplanar. FIGS. 6 and 6A illustrate examples of preferred embodiments of this bend along transition line 54. In a preferred embodiment, transition line 54 extends longitudinally across the length of the reamer blade 34. The transition line 54 is further positioned such that the width of the cutting portion 40 is greater than the width of the blade attachment portion 38. The width of the blade cutting portion 40 is defined as the distance between the transition line 54 and the outer edge of the flat portion 56. The width of the blade attachment portion 38 is defined as the distance between the transition line 54 and the bottom edge of the attachment portion 36. Alternatively, the transition line 54 may be positioned such that the width of the cutting portion 40 is less than the width of the blade attachment portion 38 it is preferred that the reamer blade 34 is bent along transition line 54 such that when each of the blades 34 is assembled in the cylindrical body 10, they are in the same orientation, such as the blade 34 orientation shown in FIGS. 8 and 9. This orientation provides for a uniform helical cutting motion as the reamer head assembly 100 (FIG. 9) rotably advances through the intramedullary space.

FIG. 6 illustrates a preferred embodiment in which the blade cutting portion 40 has a radius of curvature. This radius of curvature is defined by radius 58 which can range from about 3 mm to about 15 mm. In addition to the radius of curvature, cutting portion 40 is further bent along transition line 54 by angle 62. Angle 62 as illustrated in FIGS. 6 and 6B is defined as the sweep between the tangent plane that intersects edge 66 and blade surface 48, and the side planar surface of blade attachment portion 38. It is preferred that angle 62 ranges from about 85° to about 175°. More preferably, angle 62 ranges from about 145° to about 165° and most preferably from about 150° to about 160°.

In an alternately preferred embodiment, as illustrated in FIG. 6A, reamer blade 34 has a cutting portion 40 with an angled plane. Unlike the previous embodiment shown in FIG. 6, the plane of the cutting portion 40 is not curved. The cutting portion 40 of the embodiment shown in FIG. 6A, is fabricated with a straight edge that is bent along transition line 54. This bend angle 62 is measured between the surface of the blade cutting portion 40 and surface 42 of the blade attachment portion 38. It is preferred that angle 62 range from about 85° to about 175°. More preferably angle 62 ranges from about 145° to about 165° and most preferably from about 150° to about 160°.

Figure 7:
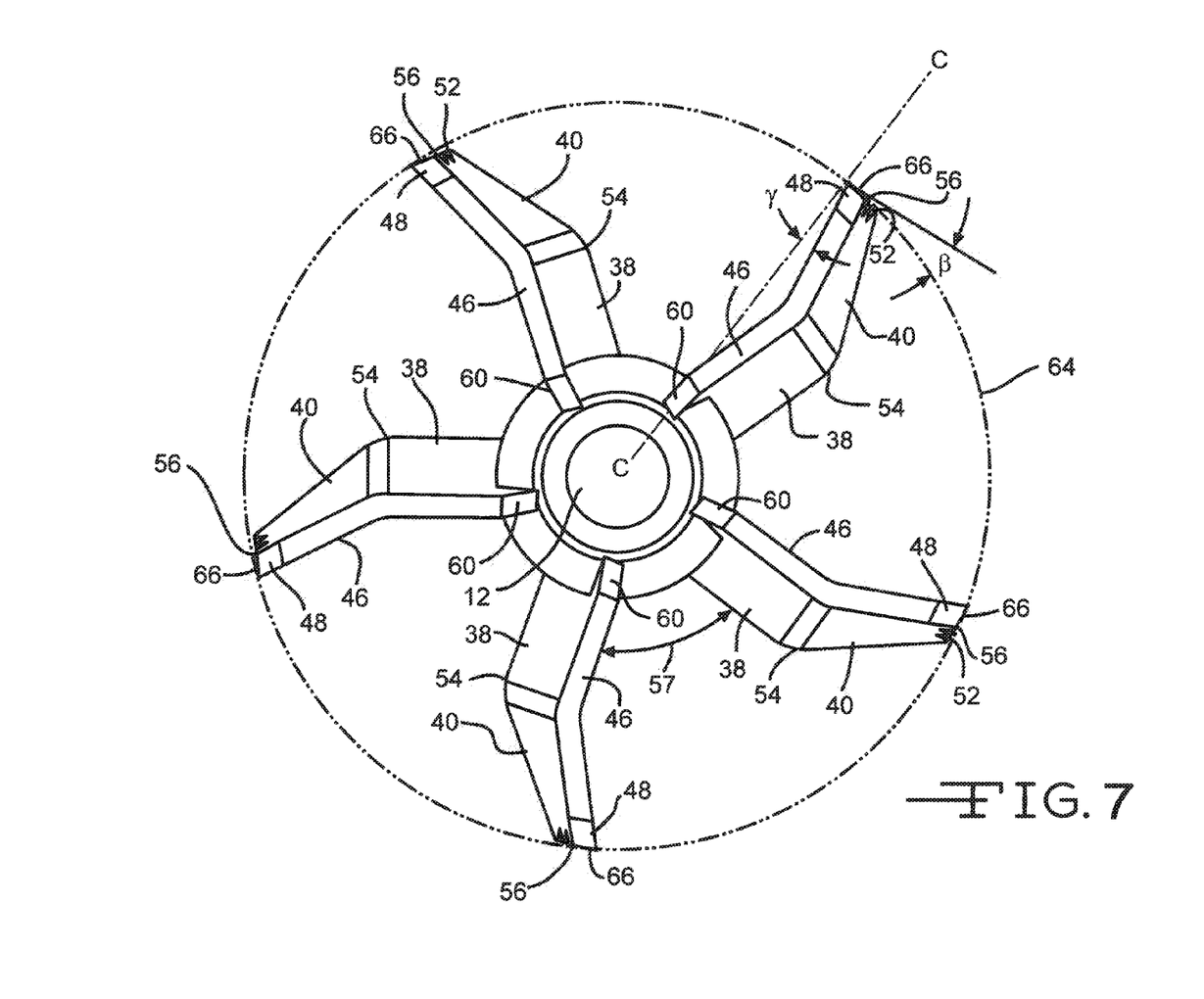
FIG. 7 is an illustration of the reamer blade assembly of the present invention taken from the distal end portion.

As shown in FIGS. 6, 6A and 7, the quality of the reamed intramedullary space is largely dependent upon additional reamer blade 34 parameters. These additional parameters include a cutting edge angle $\alpha$, a relief angle $\beta$, a rake angle $\gamma$, and the relationship between these parameters. A reamer blade 34 with an optimized cutting edge angle $\alpha$, relief angle $\beta$, and rake angle $\gamma$ produce a reamed cavity with a desirable smooth bore surface. If the reamer blades 34 are not designed with these optimized parameters, a reamed cavity with an undesirable lobed surface is created. A lobed cavity surface is one in which the surface has lumps or has a scalloped surface.

Cutting edge angle $\alpha$, illustrated in FIGS. 6 and 6A, is the clearance between the side edge 66 of the bone cutting surface 48 and planar portion 56. More precisely, angle $\alpha$ is measured between the planar face of edge 66 and a tangent line to the point formed by edge 66 of the inner surface of planar portion 56. Preferably cutting edge angle $\alpha$ ranges from about 1° to about 50°. Relief angle $\beta$, illustrated in FIG. 7, is measured between the intersection of the tip of relieved side edge surface 66 and a tangential plane. More precisely, relief angle $\beta$ is measured between a tangent line to the point formed by the edge 66 of the inner surface of planar portion 56 and an imaginary annular line 64 formed by the cutting action of the reamer blade 34. Rake angle $\gamma$, also illustrated in FIG. 7, is measured between perpendicular line C-C and the tangent line formed between the intersection of the point formed by the edge 66 of the inner surface of the planar portion 56 and the bone cutting surface 48. The bone cutting surface 48 and side edge 66 determines the diameter of the cavity bore 64.

In a preferred embodiment shown in FIG. 7, relief angle $\beta$ ranges from about 1° to about 25°. More preferably, relief angle $\beta$ ranges from about 5° to about 15°. It is important that the relief angle $\beta$ is not zero or negative. A negative relief angle $\beta$ is an angle in which the flat portion 56 exceeds past side edge 66 of the bone cutting surface 48. In other words, a negative relief angle $\beta$ is a reamer blade 34 with the flat portion 56 that extends past the reamed bore diameter 64. A negative relief angle $\beta$ is not desired because it creates a cavity bore 64 with a lobed inside finish. It is desirable to have a positive relief angle $\beta$ that results in a reamed bore with a smooth internal surface.

In addition to relief angle $\beta$, rake angle $\gamma$ is also an important parameter of the present invention. Rake angle $\gamma$ is a measure in which the blade cutting portion 40 deviates from the plane of the blade attachment portion 38. As shown in FIG. 7, rake angle $\gamma$ is specifically defined as the angle between the intersection of the distal end of the bone cutting surface 48 and perpendicular axis C-C which extends from the cylindrical body 10. It is preferred that rake angle $\gamma$ ranges from about 5° to about 25°. It is more preferred that rake angle $\gamma$ range from about 12° to about 15°. Rake angle $\gamma$ is a measure of the aggressiveness of the cut. A larger rake angle $\gamma$ increases the aggressiveness of the cut whereas a smaller rake angle $\gamma$ angle produces a less aggressive cut.

FIG. 7 illustrates the reamer head assembly 100 from the perspective view point, of the distal end 14, looking down its longitudinal axis. As the illustration shows, reamer blades 34 are attached to the cylindrical body 10. Each reamer blade 34 is positioned such that they are oriented in the same direction. Each blade 34 is positioned into each slot 20 with the forward cutting surface 46 and the bone cutting surface 48 facing towards the distal end 14. The rearward relief surface 50 is positioned facing the proximal end 16. In addition, it is preferred that each reamer blade is bent about transition line 54 in the same direction with about the same degree of angle 62. Although it is contemplated that the reamer 300 (FIG. 10) may be constructed with one or more reamer blades 34 with dissimilar bend orientations that may not necessarily have the same degree of angle 62.

Figure 8:
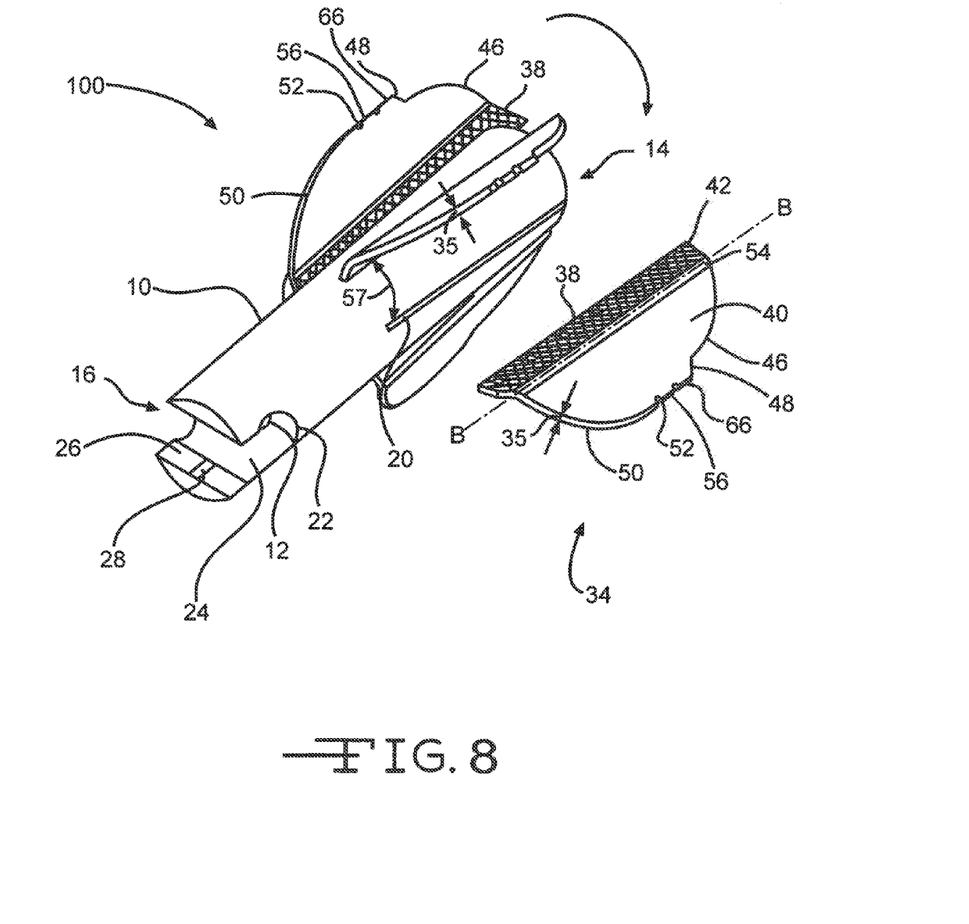
FIGS. 8 and 9 are respective dissembled and assembled perspective views of the reamer blade assembly of the present invention.

FIG. 8 illustrates a fully assembled reamer head assembly 100 of the present invention. As shown, each reamer blade 34 is positioned in their respective slot 20. In a preferred embodiment, the blade attachment portion 38 is positioned within the slot 20 such that the cutting portion 40 is bent about transition line 54 in a clockwise position. Alternatively, the reamer blades 34 could also be positioned with the cutting portion 40 bent in a counterclockwise orientation. However oriented, either in a clockwise or counter clockwise orientation, it is preferred that each reamer blade 34 is positioned into a slot 20 such that ridge 54 is bent with a similar angle 62. This preferred orientation creates a desirable helical rotation as the reamer blade 34 penetrates through the intramedullary space. Furthermore as illustrated in FIG. 8, each reamer blade 34 is positioned with its forward cutting surface 46 facing toward the distal end 14 of the reamer blade assembly 100.

In a preferred embodiment shown in FIG. 8, each reamer insert blade 34 is positioned from adjacent insert reamer blades 34 by a separation distance 57. This separation distance 57 is dependent on the number of insert blades 34 that are attached to the cylindrical body 10. The more blades 34 that are attached to the body 10, the smaller the separation distance 57. Given a typical configuration of five insert, reamer blades 34, the separation distance ranges from about 0.3 mm to about 15.0 mm depending on the diameter of the cylindrical body 10.

The separation distance 57 enables the surgeon to "lump" reamer sizes. When a reamer size is "jumped", the next incremental reamer diameter size is bypassed for a reamer with an even larger diameter. For example, during a reaming procedure, reamers of incremental sizes on the order of about 0.5 mm are typically inserted to enlarge the intramedullary space. By "jumping" reamer sizes, the surgeon can reduce the number of reaming iterations which reduces procedural time and minimizes patient trauma. With the reamer 300 of the present invention, the surgeon can bypass incremental reamer diameters of about 1.0 mm or more.

In addition, the separation distance 57 provides an opening or separation area between reamer blades 34 within which intramedullary debris can freely flow. Designing the present invention with an optimized separation distance 57 reduces the interference resistance and back pressure allowing debris to easily flow over the cylindrical body 10 between the insert reamer blades 34. Unlike previous reamer designs, the reamer 300 of the present invention has a separation area that is bounded by the outer surface 18 of the cylindrical body 10 and opposing reamer insert blades 34. The insert reamer blades 34 allow for a maximized separation area between adjacent blades 34 that is not obstructed by a portion of the reamer cutting head body of prior designs. Furthermore, notch 52 breaks up debris as it passes over the cylindrical body 10, further improving reamer efficiency.

The optimized separation area is given by the generalized equation:

$$\frac{\left[\begin{array}{c}\text{Cavity Cross Sectional Area} - \\ \text{Reamer Cross Sectional Area}\end{array}\right]}{\text{Number of Insert Blades}} \qquad \text{(Eq. 1)}$$

Where the cavity cross sectional area is the cross sectional area of the cavity formed by reamer 300 and the reamer cross sectional area is the combined cross-sectional areas of the cylindrical body 10 and blades 34. The number of insert blades is the number of insert reamer blades 34 that are attached to the cylindrical body 10. Therefore, by optimally spacing the insert reamer blades 34 around the body 10, an increased amount of intramedullary debris can be removed efficiently. Such improved efficient debris removal improves the efficiency of the reamer tool which results in minimized procedural times and less trauma to the patient.

Figure 9:
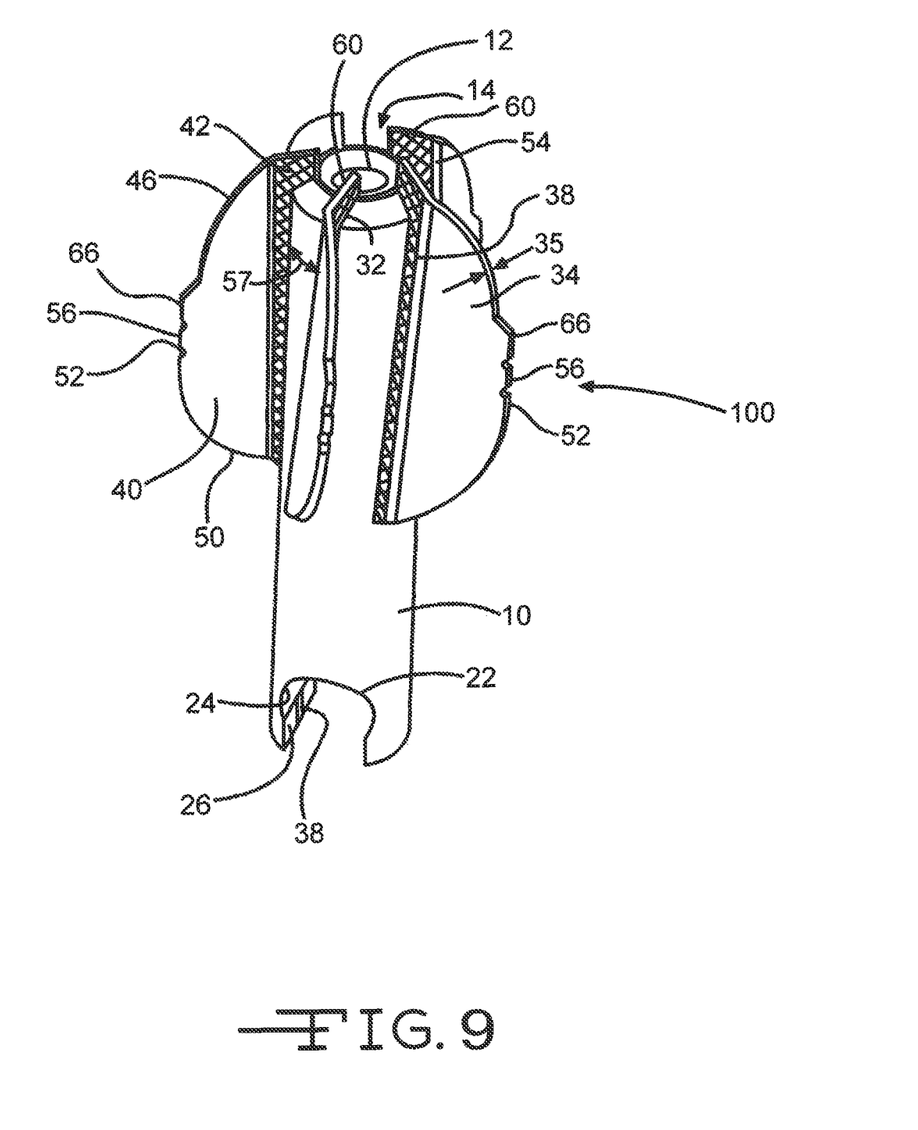

FIG. 9 illustrates an additional view of the distal end 14 of the reamer blade assembly 100. As shown, each reamer blade 34 is positioned into a slot 20. The example shown in FIG. 9 illustrates a preferred embodiment of the compound angles 30, 32 of the present invention. As shown, the blade attachment portion edge 60 is at a preferred angle of about 10° in end slot 32 and the attachment portion edge 36 is at a preferred angle of about 20°. The compound angles 30, 32 of the slot 20 help distribute the load into the cylindrical body 10 while allowing the diameter of the cylindrical body 10 to be minimized. This allows the reamer blades 34 to present a desirable helical flute pattern using simple angles for assembly.

In a preferred embodiment shown in FIG. 9, the attachment portion edge 60 and forward cutting edge 46 is shown extending past the distal end 14. Having the reamer 300 with a portion of blade 34 extending past the distal end 14, as shown in FIGS. 8-11, provides the reamer 300 with front cut capability. The forward blade design advances the blade 34 attack angle which enhances the ability of the reamer 300 to jump reamer sizes. In an alternately preferred embodiment, the attachment portion edge 60 is flush with the distal end 14 of the reamer blade assembly 100. Alternatively, reamer 300 can also be designed with a portion of the distal end 14 of the cylindrical body 10 extending past the distal end of the insert reamer blades 34. Such an alternate design with an extended cylindrical distal portion 14 provides for an insertion guide into the intramedullary space.

FIG. 10 illustrates a preferred embodiment of the reamer shaft 200 of the present invention. As shown, the reamer shaft 200 is comprised of a coupling portion 212 that is in fluid communication with a tube 210. In a preferred embodiment, the coupling portion 212 is comprised of a male dovetail end 214 and flat surface 216. The male dovetail end 214 is designed to mate with the corresponding female radius 24 and flats 26 located at the proximal end 16 of the cylindrical body 10.

When connecting the reamer head assembly 100 to the reamer shaft 200, the male dovetail end 214 slides into the female radius 24. It is preferred that the cylindrical body passageway 12 aligns with the shaft passageway 218 when connecting the reamer head assembly 100 to the shaft 200. It is preferred that the shaft tube 210 is made from a pultruded thermoset polymeric material that can withstand at least 5 N-M of torque. Pultrusion as defined herein is the process by which elongated shapes of polymer are produced. The pultrusion process involves pulling a liquid mixture of polymeric materials and associated resins and chemicals through a die in a continuous manner. Once the reamer shaft 200 is attached, the reamer 300 can be manipulated by hand or alternatively be powered by a motor. In an alternately preferred embodiment, a motor (not shown) can be connected to the reamer assembly 100 to power rotation of the blades 34. A motorized shaft (not shown) can be inserted through the shaft passageway 218 and connected to the reamer head assembly 100. Alternatively, a motor (not shown) can be connected to the shaft 200 to provide blade 34 rotation.

As previously mentioned, the present invention is assembled using an induction bonding process. In a preferred method, each reamer blade 34 is slid into place in a slot 20 of the cylindrical body 10. Once the blades 34 are in position, a heat source, emanating from a radio frequency energy source, is applied to the assembly 100 to heat up the blades 34. The application of the radio frequency energy to the blades 34 causes the material of the cylindrical body 10 to melt. The material of the cylindrical body 10 flows onto the surface 42 of the blade attachment portion 38 and through the engagement openings 44. This creates a fluid connection integrating the reamer blades 34 with the cylindrical body 10. Once the material of the cylindrical body 10 solidifies, the reamer blades 34 are securely locked into place.

In a preferred embodiment, a radio frequency induction power supply (not shown) with a work head and coil operating at a frequency range of about 100 to about 450 Khz is used to inductively weld the insert blades 34 to the cylindrical body 10. The preferred welding time of the inductive bonding process is about 1 to about 10 seconds. The application of this electrical energy to the reamer blades 34 elevates the blade 34 temperature to effectively melt the surrounding material of the cylindrical body 10. These elevated temperatures preferably range from about 100° C. to about 500° C. Alternately, a heat source such as an electromagnetic current, flame or heater could also be targeted to the reamer blades 34 to elevate their temperature.

Furthermore it is contemplated that the reamer blades 34 could also be attached to the cylindrical body 10 through other bonding means. These alternately preferred bonding means include, but are not limited to, the use of adhesives, insert molding, over-molding, press fitting, and ultrasonic bonding.

The induction process provides a cost effective means of constructing the disposable intramedullary reamer 300 (FIGS. 10 and 11) of the present invention. As previously discussed, the present invention provides for a reamer 300 and fabrication process which eliminates costly traditional machining processes. In addition, the assembly fabrication process of the present invention allows for reamer designs that could not otherwise be fabricated by traditional methods. For example, the present invention enables the use of compound angles 30, 32 in the cylindrical body 10 which bends the reamer blade 34 in an angle that provides improved cutting efficiency. Such an angle would be difficult to fabricate using traditional reamer manufacturing methods. In addition, the present invention provides for an optimal blade separation distance 57 and associated blade separation area which maximizes debris flow and enhances cutting efficiency.

Alternatively the reamer head assembly 100 may be constructed with a hollow shaft tube 210 that does not comprise a coupling portion 212. Such a tube 210 can be inserted directly into the proximal end 16 of the reamer head assembly 100 such that a snug interference fit is created. As illustrated in an alternate embodiment in FIG. 11, the distal end 220 of reamer shaft tube 210 is inserted into the reamer head assembly inlet 70 located at the assembly proximal end 16. A snug interference fit is created when the reamer shaft tube 210 is inserted into inlet 70. Alternatively, the reamer shaft tube 210 can be joined to the reamer head assembly 100 through other means such as, but not limited to, over-molding, adhesive bonding, press fitting, and ultrasonic bonding.

Furthermore, the reamer head assembly 100 can also be fabricated with an integrated reamer shaft 200 in a one piece construction. In this alternatively preferred embodiment, the proximal end 16 of the cylindrical body 10 is extended such that the shaft 200 is in fluid connection with the reamer head assembly 100. The integrated reamer shaft 200 can be solid or preferably fabricated with a central passageway 218. Preferably, the shaft 200 is made from a thermoplastic polymer material having the characteristics which allow it to withstand at least 5 N-M of torque. Alternatively, the shaft 200 could also be made from a thermoset polymer material.

Thus, it has been shown that the reamer 300 of the present invention provides for a low cost flexible single use intramedullary cutting tool. The present invention does not require additional grinding or re-sharpening procedures which ensures optimal sharpness and sterilization. The features of the present invention provide for an efficient intramedullary cutting tool with an optimized cutting design that enhances reaming efficiency and effectiveness.

What is claimed is:

1. A reamer head assembly, comprising:
   a) a body comprising an annular outer surface, a proximal body end extending to a distal body end along a longitudinal axis, at least two body slots, each body slot having a slot length and a slot depth, the slots positioned within the annular outer surface of the body such that the slot length is not parallel with the longitudinal axis as it extends from the proximal body end to the distal body end, each body slot having a first slot angle measured between the slot length and the longitudinal axis of the body;
   b) at least two continuous reamer blades, each reamer blade comprising a blade length extending from a proximal blade end adjacent to the proximal body end to a distal blade end adjacent to the distal body end, wherein each reamer blade comprises a reamer blade attachment portion and a reamer blade cutting portion partitioned between the proximal and distal blade ends by a reamer blade transition line that extends along the reamer blade length; and
   c) wherein the reamer blades are positioned about the body, spaced apart from each other by a blade separation distance with a blade separation area therebetween, such that each reamer blade attachment portion is positioned within its respective body slot, the reamer blade cutting portion extending outwardly from the outer surface of the body and wherein each reamer blade is bent at an angle along the transition line such that the blade cutting portion and the blade attachment portion are not coplanar.

2. The reamer head assembly of claim 1 wherein the angle between the reamer blade attachment portion and the blade cutting portion is about 85° to about 175°.

3. The reamer head assembly of claim 1 wherein the blade separation distance ranges from about 0.3 mm to about 15.0 mm.

4. The reamer head assembly of claim 1 wherein the blade separation area is defined by:

$$\frac{[\text{Cavity Cross Sectional Area} - \text{Reamer Cross Sectional Area}]}{\text{Number of Insert Blades}}$$

wherein the cavity cross sectional area is equal to a cross sectional area of a cavity within a bone formed by the reamer head assembly, and the reamer cross sectional area is the combined cross sectional areas of the body and the reamer blades.

5. The reamer head assembly of claim 1 wherein the body slot has a second slot angle, the second slot angle measured between the slot depth and a radial axis extending perpendicularly from the longitudinal axis of the body.

6. The reamer head assembly of claim 5 wherein the first slot angle is from about 5° to about 30° and the second slot angle is from about 5° to about 45°.

7. The reamer head assembly of claim 1 wherein the cutting surface extends from a forward blade surface, located adjacent the body distal end to a rearward relief surface, located adjacent the body proximal end, a bone cutting surface disposed therebetween, the bone cutting surface having an angled surface measuring from about 40° to about 50° with respect to the longitudinal axis of the body.

8. The reamer head assembly of claim 1 wherein each reamer blade has a relief angle and a rake angle.

9. The reamer head assembly of claim 8 wherein the relief angle measures from about 1° to about 25° and the rake angle measures from about 5° to about 25°.

10. The reamer head assembly of claim 1 wherein the reamer blade is composed of a material selected from the group consisting of stainless steel, MP35N, titanium, and combinations thereof.

11. The reamer head assembly of claim 1 wherein the body is composed of a moldable biocompatible polymeric material.

12. The reamer head assembly of claim 1 wherein the proximal body end is connectable to a reamer shaft.

13. A reamer comprising:
 a) a body comprising an annular outer surface, a proximal body end extending to a distal body end along a longitudinal axis, the proximal body end connectable to a reamer shaft, at least two body slots, each slot having a slot length and a slot depth, the body slots positioned within the annular outer surface of the body such that the slot length is not parallel with the longitudinal axis as it extends from the proximal body end to the distal body end, each body slot having a first slot angle measured between the body slot length and the longitudinal axis of the body;
 b) at least two continuous reamer blades, each reamer blade having a reamer blade thickness and a reamer blade length extending from a proximal reamer blade end adjacent to the proximal body end to a distal reamer blade end adjacent to the distal body end, the reamer blades further comprising a reamer blade attachment portion and a reamer blade cutting portion partitioned between the proximal and distal reamer blade ends by a reamer blade transition line that extends parallel to the reamer blade length, each reamer blade is bent at an angle along the transition line such that the blade cutting portion and the blade attachment portion are not coplanar; and
 c) wherein the reamer blades are positioned about the body, spaced apart from each other by a blade separation distance with a blade separation area therebetween, such that the reamer blade attachment portion is positioned within its respective body slot, the reamer blade cutting portion extending outwardly from the outer surface of the body, the reamer blades further comprising a forward blade cutting surface positioned adjacent the distal body end and a rearward relief blade surface positioned adjacent the proximal body end.

14. The reamer of claim 13 wherein the angle between the reamer blade attachment portion and the blade cutting portion is about 85° to about 175°.

15. The reamer of claim 13 wherein the blade separation distance ranges from about 0.3 mm to about 15.0 mm.

16. The reamer of claim 13 wherein the body slot further comprises a second slot angle, the second slot angle measured between the slot depth and a radial axis extending from the longitudinal axis of the body.

17. A reamer head assembly comprising:
 a) a body comprising an annular outer surface, a proximal body end extending to a distal body end along a longitudinal axis, at least two body slots, each slot having a slot length and a slot depth positioned within the annular outer surface of the body such that the slot length is not parallel with the longitudinal axis as it extends from the proximal body end to the distal body end, the slot depth penetrating through a portion of the outer surface of the body, each body slot further comprising a first slot angle and a second slot angle, the first slot angle measured between the slot length and the longitudinal axis, the second slot angle measured between the slot depth and a radial axis extending perpendicularly from the longitudinal axis;
 b) at least two continuous reamer blades, each reamer blade comprising a blade length extending from a proximal blade end adjacent to the proximal body end to a distal blade end adjacent to the distal body end, wherein each reamer blade comprises a reamer blade attachment portion and a reamer blade cutting portion partitioned between the proximal and distal blade ends by a reamer blade transition line that extends along the reamer blade length, each reamer blade is bent at an angle along the transition line such that the blade cutting portion and the blade attachment portion are not coplanar; and
 c) wherein the reamer blades are positioned about the body, spaced apart from each other by a blade separation distance with a blade separation area therebetween, such that the reamer blade attachment portion is positioned within its respective body slot, the reamer blade cutting portion extending outwardly from the outer surface of the body.

18. The reamer head assembly of claim 17 wherein the blade separation distance ranges from about 0.3 mm to about 15.0 mm.

19. The reamer head assembly of claim 17 wherein the blade separation area is defined by:

$$\frac{[\text{Cavity Cross Sectional Area} - \text{Reamer Cross Sectional Area}]}{\text{Number of Reamer Blades}}$$

wherein the cavity cross sectional area is equal to a cross sectional area of a cavity within a bone formed by the reamer head assembly, and the reamer cross sectional area is the combined cross sectional areas of the body and the reamer blades.

20. The reamer head assembly of claim 17 wherein the first slot angle ranges from about 5° to about 30° and the second slot angle ranges from about 5° to about 45°.

21. The reamer head assembly of claim 17 wherein each reamer blade has a relief angle that ranges from about 1° to about 25° and a rake angle that ranges from about 5° to about 25°.

22. A reamer head assembly comprising:
a) a body comprising an annular outer surface, a proximal body end extending to a distal body end along a longitudinal axis, at least two body slots, each slot having a slot length and a slot depth positioned within the annular outer surface of the body such that the slot length is not parallel with the longitudinal axis as it extends from the proximal body end to the distal body end, the slot depth penetrating through a portion of the outer surface of the body, each body slot further comprising a first slot angle and a second slot angle, the first slot angle measured between the slot length and the longitudinal axis, the second slot angle measured between the slot depth and a radial axis extending perpendicularly from the longitudinal axis;
b) at least two continuous reamer blades, each reamer blade comprising a reamer blade attachment portion and a reamer blade cutting portion partitioned therebetween by a reamer blade transition line that extends along a reamer blade longitudinal axis;
c) each reamer blade positioned about the cylindrical body, spaced apart from adjacent reamer blades by a blade separation distance and a blade separation area therebetween, such that the reamer blade attachment portion is positioned within its respective body slot; and
d) wherein each reamer blade is bent at an angle along the reamer blade transition line such that the reamer blade cutting portion and the reamer blade attachment portion are not coplanar.

23. The reamer head assembly of claim 22 wherein the angle between the reamer blade attachment portion and the blade cutting portion is about 85° to about 175°.

24. The reamer head assembly of claim 22 wherein the blade separation distance ranges from about 0.3 mm to about 15.0 mm.

25. The reamer head assembly of claim 22 wherein the blade separation area is defined by:

$$\frac{[\text{Cavity Cross Sectional Area} - \text{Reamer Cross Sectional Area}]}{\text{Number of Reamer Blades}}$$

wherein the cavity cross sectional area is equal to a cross sectional area of a cavity within a bone formed by the reamer head assembly and the reamer cross sectional area is the combined cross sectional areas of the body and the reamer blades.

26. The reamer head assembly of claim 22 wherein the first slot angle ranges from about 5° to about 30° and the second slot angle ranges from about 5° to about 45°.

27. The reamer head assembly of claim 22 wherein each reamer blade has a relief angle that ranges from about 1° to about 25° and a rake angle that ranges from about 5° to about 25°.

28. The reamer head assembly of claim 22 wherein a bone cutting surface resides between the forward cutting surface and the rearward cutting surface, the bone cutting surface further positioned such that it faces toward the distal end portion of the reamer head assembly.

29. The reamer head assembly of claim 1 wherein the annular outer surface of the body is cylindrical.

30. The reamer head assembly of claim 1 wherein the reamer blade cutting portion has a helical shape from the proximal blade end to the distal blade end.

* * * * *

UNITED STATES PATENT AND TRADEMARK OFFICE
CERTIFICATE OF CORRECTION

| | | |
|---|---|---|
| PATENT NO. | : 8,454,608 B2 | Page 1 of 1 |
| APPLICATION NO. | : 12/961565 | |
| DATED | : June 4, 2013 | |
| INVENTOR(S) | : Victor et al. | |

It is certified that error appears in the above-identified patent and that said Letters Patent is hereby corrected as shown below:

On the Title Page, Column 1 item [75] (Inventors, line 2) delete ";W." and insert --M.--

In the Claims

Column 13, line 6, Claim 4, delete "Insert" and insert --Reamer--

Signed and Sealed this
Third Day of June, 2014

Michelle K. Lee
*Deputy Director of the United States Patent and Trademark Office*